United States Patent [19]

Lassalle et al.

[11] Patent Number: 5,585,498
[45] Date of Patent: Dec. 17, 1996

[54] IMIDAZOLE DERIVATIVES USEFUL AS SYNTHETIC INTERMEDIATES

[75] Inventors: Gilbert Lassalle, Clamart; Thomas Purcell, Montfort l'Amaury; Daniel Galtier, Saint Cyr l'Ecole; Paul H. Williams, Paris; Frédéric Galli, La Celle Saint Cloud, all of France

[73] Assignee: Synthelabo, Le Plessis Robinson, France

[21] Appl. No.: 223,602

[22] Filed: Nov. 5, 1993

Related U.S. Application Data

[63] Continuation-in-part of Ser. No. 37,972, Mar. 29, 1993, Pat. No. 5,453,430.

[30] Foreign Application Priority Data

Mar. 30, 1992 [FR] France .................................. 92 03828

[51] Int. Cl.$^6$ .................................................. C07D 233/64
[52] U.S. Cl. ................................... 548/335.5; 548/338.1; 548/339.1
[58] Field of Search .............................. 548/338.1, 339.1, 548/335.5

[56] References Cited

FOREIGN PATENT DOCUMENTS 0008746  3/1980  European Pat. Off. .

*Primary Examiner*—Jacqueline Haley
*Attorney, Agent, or Firm*—Jacobson, Price, Holman & Stern, PLLC

[57] ABSTRACT

Compounds of formula (I)

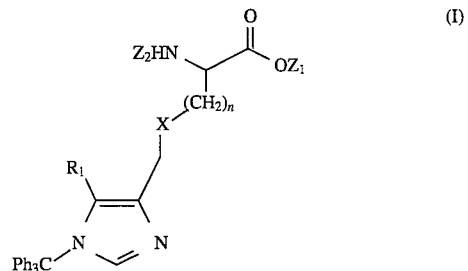

wherein $R_1$ represents either a hydrogen atom, or a $(C_1-C_4)$alkyl group,

X represents either a sulphur atom, an oxygen atom or a methylene group, $Z_1$ represents either a hydrogen atom, or a 1,1-dimethylethyl group, $Z_2$ represents either a hydrogen atom, a triphenylmethyl group, or a phenylmethoxycarbonyl group, and n=1 or 2, and addition salts to inorganic or organic acids thereof as synthetic intermediates.

7 Claims, No Drawings

IMIDAZOLE DERIVATIVES USEFUL AS SYNTHETIC INTERMEDIATES

This application is a continuation-in-part of application Ser. No. 08/037,972, filed Mar. 29, 1993, now U.S. Pat. No. 5,453,430, the disclosure of which is incorporated herein by reference.

The present invention relates to imidazole derivatives, their preparation and their utilisation as synthetic intermediates. The compounds of the invention are of formula (I)

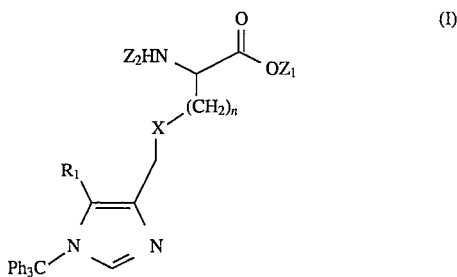

wherein $R_1$ represents either a hydrogen atom, or a $(C_1-C_4)$alkyl group,

X represents either a sulphur atom, an oxygen atom or a methylene group, $Z_1$ represents either a hydrogen atom, or a 1,1-dimethylethyl group, $Z_2$ represents either a hydrogen atom, a triphenylmethyl group, or a phenylmethoxycarbonyl group, and n=1 or 2.

The compounds of the invention possess in the central aminoacid moiety an assymetric centre of which the preferred configuration is [S].

The compounds of the invention may be in the form of free bases or addition salts to inorganic or organic acids.

In schemes 1 to 4 that follow, Ts represents a 4-(methylphenyl)sulphonyl group.

The compounds of the invention, in which X represents a methylene group, are of the formula (Ia)

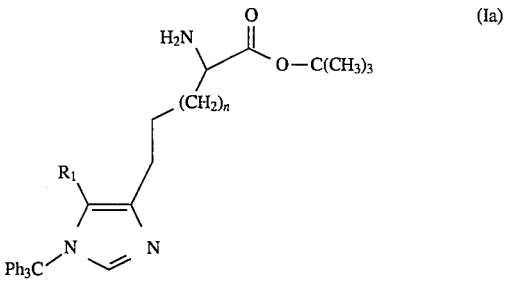

in which $R_1$ and n are as defined above; they may be synthesised as shown in scheme 1 of the following page. In the first step, an alcohol of formula (II) is allowed to react with thionyl chloride in a mixture of dimethylformamide/dichloromethane. The compound thus obtained is then allowed to react with triphenylphosphine in a solvent such as dimethylformamide or benzene, at a temperature of 80° C.; in this way the triphenylmethyl phosphonium chloride derivative of formula (III) is obtained.

In the second step, a compound of formula (III) is allowed to react with a compound of formula (IV), in a solvent such as tetrahydrofuran, in the presence of n-butyllithium at a temperature of −70° C. In this way, a compound of formula (V) is obtained in the form of a mixture of cis/trans isomers about the double bond.

In the third step, the compound (V) obtained previously is subjected to a catalytic hydrogenation in order to obtain a compound of formula (Ia). The C-terminal of a compound of formula (Ia) may be deprotected by treatment with gaseous hydrogen chloride in a solvent such as benzene.

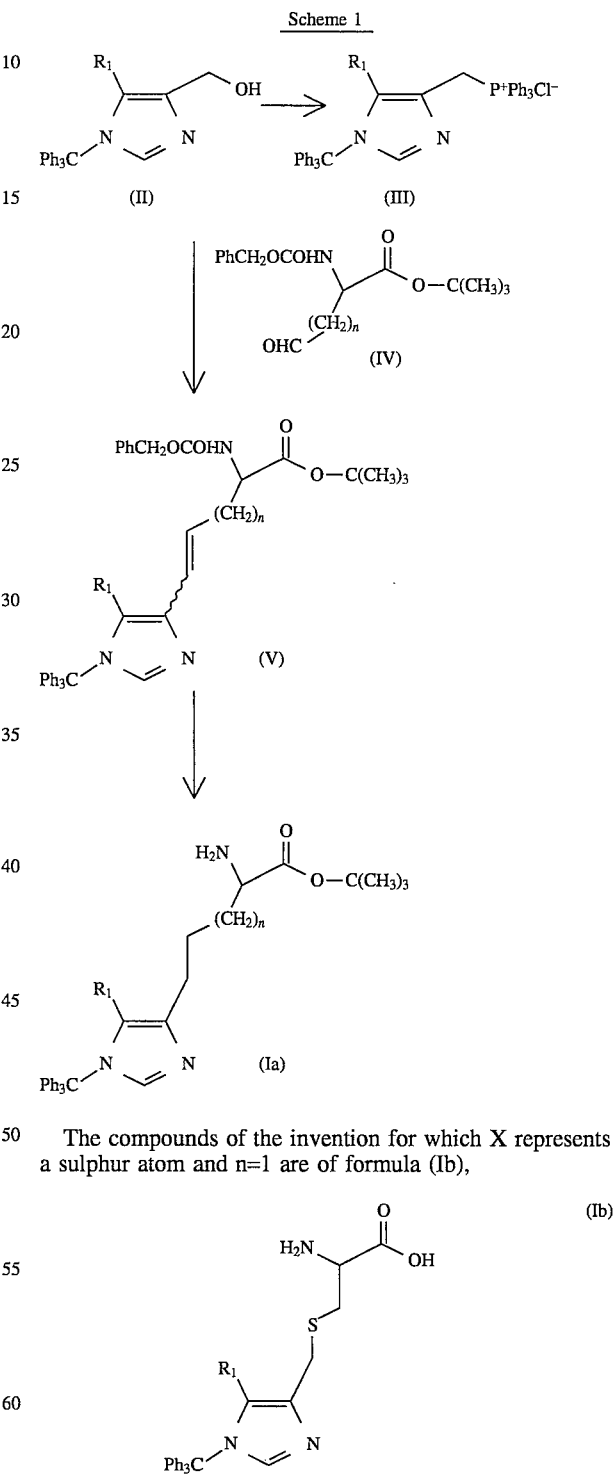

The compounds of the invention for which X represents a sulphur atom and n=1 are of formula (Ib), (Ib)

in which $R_1$ is such as described previously. The compounds of formula (Ib) may be synthesised as shown in scheme 2.

Scheme 2

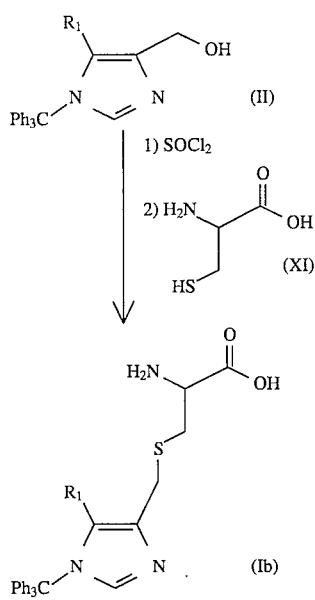

An alcohol of formula (II) is allowed to react with thionyl chloride in a mixture of dimethylformamide/dichloromethane and the compound thus obtained is allowed to react with (L)-cysteine of formula (XI) in a 1N aqueous solution of sodium hydroxide.

The compounds of the invention for which X represents a sulphur atom and n=2 are of formula (Ic)

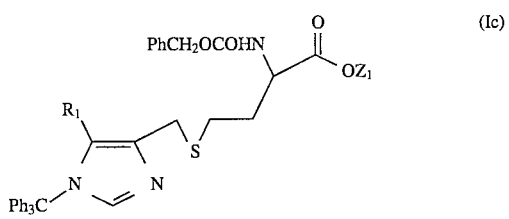

in which $R_1$ and $Z_1$ are such as is previously described.

The compounds of formula (Ic) may be synthesised as shown in scheme 3.

Scheme 3

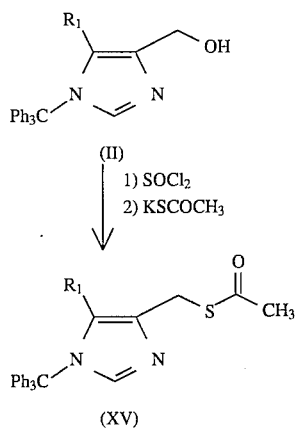

-continued
Scheme 3

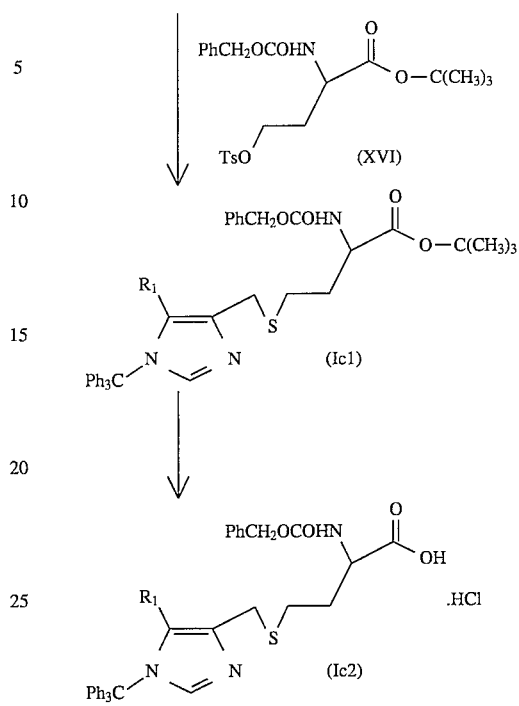

In the first step, an alcohol of formula (II) is allowed to react with thionyl chloride in a mixture of dimethylformamide/dichloromethane and the compound thus obtained is allowed to react with potassium thioacetate. In this way, a compound of formula (XV) is obtained.

In the second step, a compound of formula (XV) is allowed to react with a tosylate of formula (XVI) to provide a compound of formula (Ic1); this reaction takes place in the presence of a base such as sodium methoxide. The tosylate of formula (XVI) is obtained by the action of paratoluenesulphonyl chloride on the alcohol containing precursor of the compound of formula (IV), in the presence of a base, following the synthesis described by Valerio, R. M. et al. in Synthesis 1988, p 786.

In the third step, the C-terminal of the compound of formula (Ic1) is deprotected by treatment with hydrogen chloride gas in a solvent such as benzene, providing a compound of formula (Ic2). The N-terminal of compound of formula (Ic2) may be deprotected by catalytic hydrogenation.

The compounds of the invention for which X represents an oxygen atom are of formula (Id)

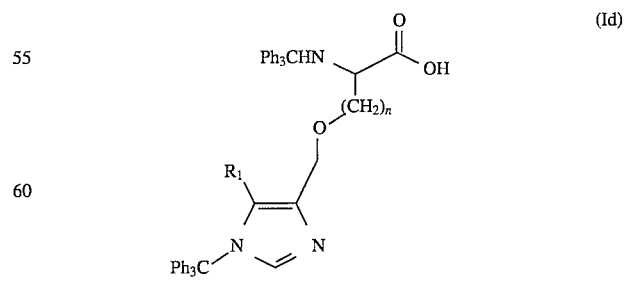

in which $R_1$ and n are such as are previously defined. The compounds of formula (Id) may be synthesised following scheme 4.

An alcohol of formula (II) is allowed to react with thionyl

Scheme 4

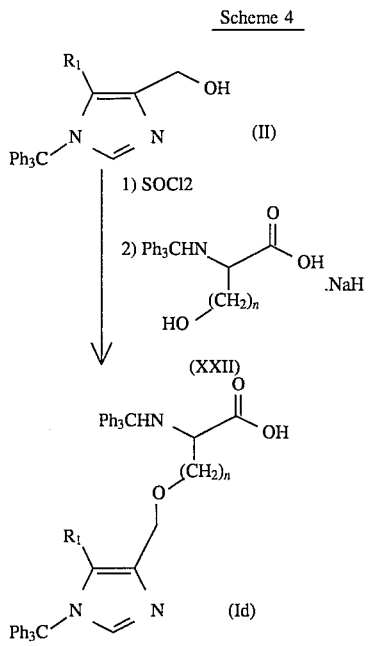

chloride in a mixture of dimethylformamide/dichloromethane; the compound thus obtained is then allowed to react with a compound of formula (XXII) after having been first allowed to react with an excess of sodium hydride in tetrahydrofuran. The N-terminal of compound of formula (Id) may be deprotected by treatment with trifluoroacetic acid in a mixture of dichloromethane/methanol.

The European patent n° 0008746 published Mar. 19, 1980, describes some $N^2$-arylsulphonyl-L-argininamide derivatives.

The starting materials are either commercially available or are described in the literature or may be prepared following described literature methods or which are known to those skilled in the art.

Hence, compounds of formula (II) are prepared by methods analogous to those described in the European patent n° 0242973 and those described by Griffith R. K. et al. in Synthesis, 1983,576.

Certain compounds of formula (IV) are described by Valerio R. M. et al. in Synthesis, 1988,786.

The compounds of formula (XXII) are described by Barlos et al. in J. Org. Chem., 1982, 47, 1324 and are treated as described by Barlos et al. in Tetrahedron, 1983, 39, 475.

The following examples illustrate the preparation of some compounds according to the invention. The elemental analyses confirm the structure of the compounds obtained.

EXAMPLE 1

1,1-dimethylethyl (S)-2-amino-5-[1-(triphenylmethyl) -1H-imidazol-4-yl]pentanoate hydrochloride 1.1 triphenyl[[(1-triphenylmethyl)-1H-imidazol-4-yl]methyl]phosphonium chloride 77.7 g (296 mmoles) of triphenylphosphine was added to a solution of 105.5 g (294 mmoles) of 4-(chloromethyl)-1-(triphenylmethyl)-1H-imidazole in 670 ml of dimethylformamide. The resulting mixture was heated at 80° C. for three hours before being allowed to cool to room temperature. The solvent then was evaporated and the crude residue taken up in ether and triturated. The precipitate was filtered and dried under vacuum over phosphorus pentoxide to provide 162 g of the title compound in the form of yellowish crystals.

Melting point=210° C. Yield=89%

1.2. 1,1-dimethylethyl (S, E)-2-[[(phenylmethoxy)carbonyl]amino]-5-[1-(triphenylmethyl)-1H-imidazol-4-yl]pent-4-enoate 50.93 g (820 mmoles) of triphenyl [[(1-triphenylmethyl)-1H-imidazol-4-yl]methyl]phosphonium chloride dissolved in 333 ml of tetrahydrofuran was placed under argon at −70° C. in a three-necked flask; 51.2 ml of a 1.6M solution of n-butyllithium in hexane (820 mmoles) was added in a dropwise fashion. After 30 minutes stirring at −70° C. the reaction medium was transferred rapidly into 270 ml of a 0.253M solution of 1,1-dimethylethyl (S)-4-oxo-2-[[(phenylmethoxy)carbonyl]amino]butanoate in tetrahydrofuran (683 mmoles) cooled to −70° C. The temperature of the reaction mixture was allowed to attain room temperature overnight before 280 ml of a saturated aqueous solution of sodium chloride was added. The aqueous phase was extracted twice with 140 ml of ethyl acetate. The combined organic phases were then dried over magnesium sulphate and evaporated to dryness. Purification was carried out using column chromatography using a hexane/ethyl acetate gradient as eluent to provide the title compound as a mixture of cis and trans olefins For the cis form:
 melting point=66° C.
 $R_f$=0.30 [hexane:ethyl acetate; 60:40 ]
For the trans form:
 $R_f$=0.15 [hexane:ethyl acetate; 60:40]
 Yield=40%

1.3. 1,1-dimethylethyl (S)-2-amino-5-[1-(triphenylmethyl)-1H-imidazol-4-yl]pentanoate hydrochloride 5.83 g (9.50 mmoles) of the cis compound obtained in 1.2 were dissolved in 120 ml of ethanol. Catalytic hydrogenation was carried out for five hours at 50 psi in the presence of palladium on charcoal as catalyst. The catalyst was filtered through a mixture of celite and silica and the solvent was evaporated to provide 4.32 g of product which was dissolved in 90 ml of a warm solution of a 0.1M hydrogen chloride in isopropanol. The solvent was evaporated and the resulting residue precipitated with ether and dried under vacuum to provide 3.62 g of title compound.

Melting point=73 ° C. Yield=73%

EXAMPLE 2

2-amino-3-[[[1-(triphenylmethyl)-1H-imidazol-4-yl]methyl]thio]propanoic acid

To a stirred solution of 2.66 g (22 mmoles) of L-cysteine in 40 ml of 1N aqueous solution of sodium hydroxide (40 mmoles) at 0° C. was added a solution of 7.2 g (20 mmoles) of 4-(chloromethyl)-1-(triphenylmethyl)-1H-imidazole in 50 ml of ethanol and 20 ml of tetrahydrofuran. The temperature was allowed to rise to room temperature and the mixture was stirred for 1 hour. The solvents were evaporated under reduced pressure and the residue was taken up in 100 ml of water and 20 ml of 1N hydrochloric acid to provide a precipitate that was filtered, washed with water, filtered and dried under vacuum to provide 8 g of title compound.

Melting point=162°–164 ° C. (decomposition) Yield=90%

EXAMPLE 3

(S) -2-[[phenylmethoxy)carbonyl]amino]-4-[[[1-(triphenylmethyl)-1H-imidazol-4-yl]methyl]thio]butanoic acid hydrochloride 3.1. 1,1-dimethylethyl (S)-2-[[(phenylmethoxy)carbonyl]amino]-4-[[[1-(triphenylmethyl)-1H-imidazol-4-yl]methyl]thio]butanoate 6 g of potassium thioacetate were added to a solution of 3.58 g (10 mmoles) of 4-(chloromethyl)-1-(triphenylmethyl)-1H-imidazole in 40 ml of ethanol under nitrogen. The reaction mixture was agitated by sonification for 15 minutes before being poured onto ether. The resulting organic phase was washed successively with water, a saturated solution of sodium hydrogen carbonate, a saturated solution of sodium chloride, before being dried over magnesium sulphate and evaporated under reduced pressure. The residue was dissolved in 100 ml of methanol degassed with nitrogen and containing 1.9 ml (10 mmoles) of a 5.3N solution of sodium methoxide. After stirring for 15 minutes, a solution of 4.63 g (10 mmoles) of 1,1-dimethylethyl (S)-4[[4-methylphenyl)sulphonyl]-2[[(phenylmethoxy)carbonyl]amino]butanecarboxylate in 40 ml of degassed methanol were added. The reaction mixture was stirred for 24 hours at room temperature and the precipitate thus obtained was evaporated, washed with methanol and then with water before being dried to provide 3 g of the title compound.

Melting point=183°–185° C. Yield=50%

3.2. (S)-2-[[phenylmethoxy)carbonyl]amino]-4-[[[1-(triphenylmethyl)-1H-imidazol-4-yl]methyl]thio]butanoic acid hydrochloride 2.5 g (3.86 moles) of the compound obtained in paragraph 3.1 was placed in 50 ml of benzene. The solution, protected from humidity, was saturated with gaseous hydrogen chloride at 0° C. for 10 minutes. The reaction mixture was stirred for 2 hours at 0° C., before being evaporated under reduced pressure to provide 2.2 g of title compound that was used as such in the next step.

Melting point=78°–82° C. Yield=91%

EXAMPLE 4

(N)-(triphenylmethyl)-(O)-[[1-(triphenylmethyl)-1H-imidazol-4-yl]methyl]-(L)serine acid 0.39 g (5.7 mmoles) of 4-(chloromethyl)-1-(triphenylmethyl)-1H-imidazole followed by 10.01 g (28.83 mmoles) of (N)-(triphenylmethyl)-(L)-serine was added to a stirred suspension of 5.8 g (144.2 mmoles) of a 60% suspension of sodium hydride in 112 ml of tetrahydrofuran, at −15° C. Stirring was continued at −15° C. for 45 minutes before a further 12 g (34.6 mmoles) of 4-(chloromethyl)-1-(triphenylmethyl)-1H-imidazole were added.

The reaction mixture was stirred for 2 hours at 0 ° C., followed by 5 hours at room temperature before being cooled to 0 ° C.; then it was diluted with 200 ml of water and neutralised by adding 6.59 ml (115 mmoles) of acetic acid. The mixture was decanted and the aqueous phase collected and extracted twice with 200 ml of ethyl acetate. The organic extracts were combined, washed with approximately 300 ml of water and dried over magnesium sulphate. The solvents were evaporated and the residue purified by silica gel column chromatography using as eluent a gradient of ethanol:dichloromethane (2:98–4:96) to provide 112.82 g of title compound.

Melting point=104°–106° C. Yield=68%

The compounds of the invention are useful as substitutes for lysine and arginine in the synthesis of peptides and pseudopeptides that conform to example A described below.

Example A ethyl [2R-[1(S),2α, 4β]]-4-methyl-1-[2-[3-methyl-1,2,3,4-tetrahydroquinolin-8-yl)sulphonyl]amino]-1-oxo-5-(1H-imidazol-4-yl)pentyl]piperidine-2-carboxylate 1. 1,1-dimethylethyl (S)-2[[(3-methylquinolin-8-yl)sulphonyl]amino]-5-[1-(triphenylmethyl)-1H-imidazol-4-yl]pentanoate A solution of 1.76 g (7.28 mmoles) of 8-(chlorosulphonyl)-3-methylquinoline in 50 ml of chloroform was added to 3.8 g (7.26 mmoles) of the compound obtained in example 1.3 in the presence of 2.1 ml (14.5 mmoles) of triethylamine at 5° C. After stirring for three hours, the organic phase was separated, washed with a 0.1N solution of hydrochloric acid before being evaporated to dryness. The crude residue was purified by silica gel column chromatography using a mixture of ethanol and dichloromethane (5:95) as eluent to provide 3.6 g of title compound.

Melting point=56° C. Yield=72%

2. (S)-2[[(3-methylquinolin-8-yl)sulphonyl]amino]-5-[1-(triphenylmethyl)-1H-imidazol-4-yl]pentanoic acid Gaseous hydrogen chloride was bubbled for 15 minutes into a solution of 2.33 g (3.39 mmoles) of the compound obtained in the previous step in 34 ml of benzene at 0° C., under nitrogen. The reaction medium was allowed to attain room temperature and was stirred for a further two hours. The solvent was evaporated under vacuum and the residue purified by silica gel column chomatography using a mixture of ethanol and dichloromethane (20: 80) as eluent to provide 1.42 g of title compound in the form of a whitish powder.

Melting point=170° C. Yield=66%

3. ethyl [2R-[1(S),2α, 4β]]-4-methyl-1-[2-[3-methylquinolin-8-yl)suphonyl]amino]-1-oxo-5-[1-(triphenylmethyl)-1H-imidazol-4-yl]pentyl]piperidin-2-carboxylate 1.56 g (3.53 mmoles) of [(benzotriazol-1-yl)oxy]tris(dimethylamino)phosphonium hexafluorophosphate, 0.78 ml (7.06 mmoles) of N-methylmorpholine, 0.61 g (3.57 mmoles) of ethyl (2R-trans)-4-methylpiperidine-2-carboxylate in 30 ml of dichloromethane were successively added to a suspension of 2.23 g (3.53 mmoles) of the compound obtained in previous step in 50 ml of acetonitrile, at 0° C. under nitrogen. The reaction medium was allowed to attain room temperature before being stirred for 5 hours. The reaction medium was hydrolysed with a saturated solution of sodium chloride and extracted with chloroform. The organic extracts were then washed successively with a 0.1N solution of hydrochloric acid, a saturated solution of sodium hydrogen carbonate, water and finally with a saturated solution of sodium chloride before being dried over magnesium sulphate and evaporated. The crude residue obtained was purified by silica gel column chromatography using a mixture of ethanol and dichloromethane (5:95) as eluent to provide 1.94 g of product.

$R_f$=0.68 (dichloromethane:ethanol; 95:5) Yield=70%

4. ethyl [2R-[1(S),2α, 4β]]-4-methyl-1-[2-[3-methyl-1,2,3,4-4-tetrahydroquinolin-8-yl)sulphonyl]amino]-1-oxo-5-(1H-imidazol-4-yl)pentyl]piperidine-2-carboxylate 17 ml of acetic acid was added to a solution of 1.94 g (2.47 mmoles) of the ester obtained in the previous step in 70 ml of ethanol. Catalytic hydrogenation was then carried out in the presence of palladium on charcoal, at 80° C. for 6 hours. The mixture was filtered and the solvent evaporated. The residue obtained was taken up in 1N hydrochloric acid, washed with ether and extracted with ethyl acetate. The combined organic phases were evaporated to provide 1.05 g of title compound.

Melting point=104° C. (hydrochloride) Yield=78%

$[\alpha]_D^{20}$=+101° (c=0.2; methanol)

These peptides and pseudopeptides may be used in any clinical indications connected with thrombosis or in cases where thrombotic complications may arise, such as is described in the European patent application n° 93400772.5.

We claim:

1. A compound of formula (I) having a central amino acid part

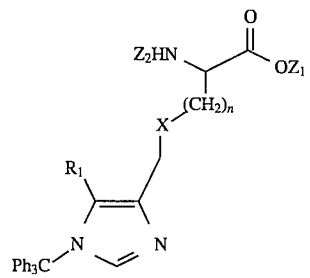

wherein

R₁ represents either a hydrogen atom or a (C₁–C₄)alkyl group,

X represents either a sulphur atom, an oxygen atom, or a methylene group, $Z_1$ represents either a hydrogen atom or a 1,1-dimethylethyl group, $Z_2$ represents either a hydrogen atom, a triphenylmethyl group, or a phenylmethoxycarbonyl group, and n=1 or 2, or an inorganic or organic acid addition salt to thereof.

2. The compound according claim 1 wherein the configuration in the central amino acid part is [S].

3. The compound according claim 1 having the formula

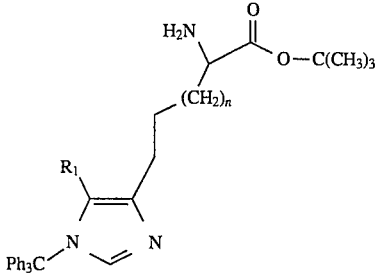

wherein R₁ and n are defined as in claim 1.

4. The compound according to claim 1 having the formula

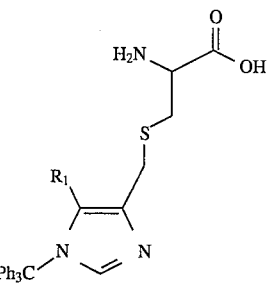

wherein R₁ is defined as in claim 1.

5. The compound according to claim 1 having the formula

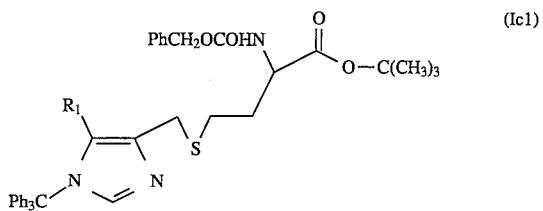

wherein R₁ is defined as in claim 1.

6. The compound according to claim 1 having the formula

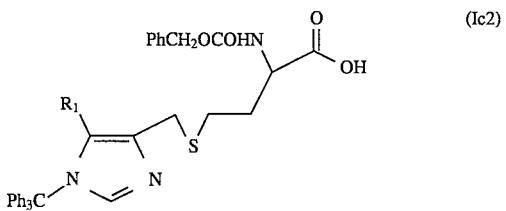

wherein R₁ is defined as in claim 1.

7. The compound according to claim 1 having the formula

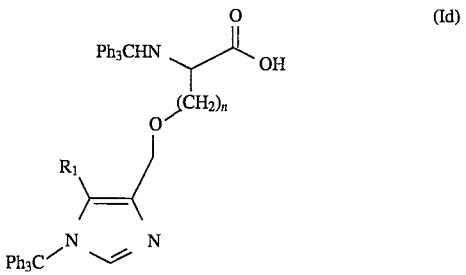

wherein R₁ and n are defined as in claim 1.

* * * * *